United States Patent [19]

Aumüller

[11] Patent Number: 5,714,611

[45] Date of Patent: Feb. 3, 1998

[54] PREPARATION OF N,N'-BRIDGED BISTETRAMETHYLPIPERIDINYL COMPOUNDS

[75] Inventor: Alexander Aumüller, Neustadt, Germany

[73] Assignee: BASF Aktiengesellschaft, Ludwigshafen, Germany

[21] Appl. No.: 669,318

[22] PCT Filed: Jan. 20, 1995

[86] PCT No.: PCT/EP95/00205

§ 371 Date: Jul. 9, 1996

§ 102(e) Date: Jul. 9, 1996

[87] PCT Pub. No.: WO95/21157

PCT Pub. Date: Aug. 10, 1995

[30] Foreign Application Priority Data

Feb. 2, 1994 [DE] Germany .................. 44 03 085.1

[51] Int. Cl.⁶ .................................................. C07D 211/46
[52] U.S. Cl. .................. 546/188; 546/19; 546/256; 546/261
[58] Field of Search .................. 546/19, 188, 256, 546/261

[56] References Cited

U.S. PATENT DOCUMENTS 3,940,363  2/1976  Murayama et al. .................. 524/102

Primary Examiner—C. Warren Ivy
Assistant Examiner—Garth M. Dahlen
Attorney, Agent, or Firm—Oblon, Spivak, McClelland, Maier & Neustadt, P.C.

[57] ABSTRACT

N,N'-bridged bistetramethylpiperidinyl compounds of Formula I

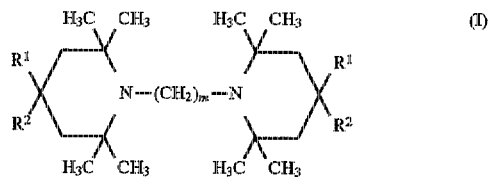

useful as light stabilizers and stabilizers for organic material which are prepared starting from tetramethylpiperidinyl compounds of Formula II

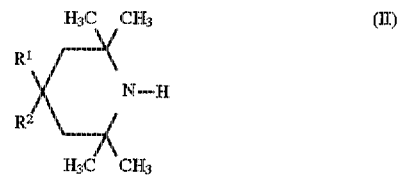

by reacting a compound of Formula II with a cyclic carbonate of Formula III.

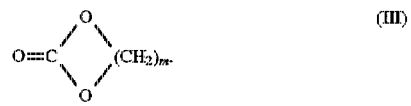

8 Claims, No Drawings

PREPARATION OF N,N'-BRIDGED BISTETRAMETHYLPIPERIDINYL COMPOUNDS

This application is a 371 of PCT/EP95/00205, Jan. 20, 1995.

The present invention relates to an improved process for the preparation of N,N'-bridged bistetramethylpiperidinyl compounds of the general formula I

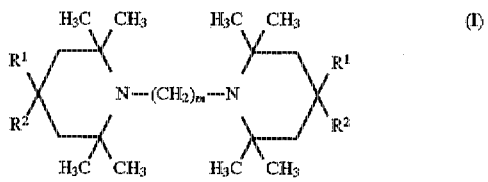

where m is 2 or 3 and the two pairs of radicals $R^1/R^2$ are identical or different and may have the following meanings:

(a)

$R^1$ is hydrogen and $R^2$ is a group of the formula —A—$R^3$, where

A is oxygen or a bridging member of the formula —$NR^4$—, —$NR^5$—CO—, —O—CO—, —O—CO—$NR^5$— or O—CO—O—, $R^3$ is hydrogen or $C_1$–$C_{20}$-alkyl which may be interrupted by up to 10 non-neighboring oxygen atoms or bridging members of the formula —$NR^4$— and by up to 3 carbonyl groups, $C_2$–$C_{20}$-alkenyl, $C_3$–$C_{12}$-cycloalkyl which may be substituted by up to 3 $C_1$–$C_4$-alkyl groups, phenyl which may be substituted by up to 3 $C_1$–$C_6$-alkyl groups or hydroxyl groups, $C_7$–$C_{18}$-phenylalkyl which may be substituted by up to 3 $C_1$–$C_4$-alkyl groups or hydroxyl groups, $C_6$–$C_{18}$-cycloalkylalkyl which may be substituted by up to 3 $C_1$–$C_4$-alkyl groups, or a five-membered or six-membered unsaturated or saturated heterocyclic ring having up to 3 hetero atoms selected from the group consisting of nitrogen, oxygen and sulfur, which may additionally be benzofused and substituted by up to 3 $C_1$–$C_6$-alkyl groups or hydroxyl groups, with the proviso that $R^3$ is not hydrogen if A is the bridging member —$NR^4$—, $R^4$ is $C_1$–$C_{20}$-alkyl, $C_2$–$C_{20}$-alkenyl, $C_3$–$C_{12}$-cycloalkyl which may be substituted by up to 3 $C_1$–$C_4$-alkyl groups, $C_7$–$C_{18}$-phenylalkyl which may be substituted by up to 3 $C_1$–$C_4$-alkyl groups, or $C_6$–$C_{18}$-cycloalkylalkyl which may be substituted by up to 3 $C_1$–$C_4$-alkyl groups and $R^5$ is hydrogen or $C_1$–$C_4$-alkyl;

(b)

$R^1$ is hydrogen and $R^2$ is $C_1$–$C_6$-alkoxycarbonyl-$C_1$–$C_{20}$-alkyloxy or $C_1$–$C_6$-alkoxycarbonyl-$C_2$–$C_{20}$-alkenyloxy;

(c)

$R^1$ and $R^2$ are each a group of the formula —O—$R^6$, where the two radicals $R^6$ are identical or different and are each $C_1$–$C_{20}$-alkyl or $C_2$–$C_{20}$-alkenyl, which may be substituted by up to 3 hydroxyl groups, and may be linked to form a 1,3-dioxane or a 1,3-dioxolane ring;

(d)

$R^1/R^2$ is the carbonyl oxygen atom of a piperidone ring, where these oxygen atoms may furthermore be etherified by groups of the structure $R^4$ to form the corresponding enol structure on the piperidone ring;

starting from tetramethylpiperidinyl compounds of the general formula II

Since some of the compounds I are novel substances, the present invention furthermore relates to these novel substances and to their use as light stabilizers and stabilizers for organic material. The present invention also relates to a process for the preparation of N,N'-bridged bistetramethylpiperidinyl esters.

Processes for the preparation of N-ethylene-bridged tetraalkylpiperidines are known. Thus, L.M. Kostochka, A.M. Belostotskii and A.P. Skoldinov, in Khim. Geterots. Soedinenii 1981, 1694–1695 (1) and Khim. Geterots. Soedinenii 1982, 1657–1661 (2), describe the photochemical dimerization of 1,2,2,6,6-pentamethylpiperidin-4-ol to give N,N'-ethylene-bridged bis-2,2,6,6-tetramethylpiperdin-4-ol (compound I in which m is 2, $R^1$ is H and $R^2$ is OH). In addition to an unsatisfactory yield, however, this method has further disadvantages. Thus, many byproducts are formed and necessitate expensive purification. The exposure to light is technically complicated and hence uneconomical. For the preparation of the bridged product, the N-methylated derivative must first be prepared in an additional stage from the industrially readily available 2,2,6,6-tetramethylpiperidin-4-ol.

Example 1 of German Laid-Open Application DOS 2,338,076 (3) describes the preparation of 1,2-bis(4-benzoyloxy-2,2,6,6-tetramethylpiperidino)ethane by reacting N-unsubstituted 4-benzoyloxy-2,2,6,6-tetramethylpiperidine with 1,2-dibromoethane. This procedure has the serious disadvantage that the highly toxic 1,2-dibromoethane is used as a reagent. Furthermore, the subsequent expensive working up of the reaction mixture by extraction with benzene (which is likewise toxic), washing, evaporating down, washing again and recrystallizing suggests that this reaction too is nonselective with respect to the desired product. The bridged piperidine derivatives stated in (3) are recommended as light and heat stabilizers for synthetic polymers.

It is an object of the present invention to provide a process which provides N-ethylene- or N-propylene-bridged tetramethylpiperidine compounds in an economical manner in high yield and selectivity while avoiding the use of toxic haloalkanes.

We found that this object is achieved by a process for the preparation of the N,N'-bridged bistetramethylpiperidine compounds I defined at the outset starting from the tetramethylpiperidine compounds II stated at the outset, which comprises reacting a compound II with a cyclic carbonate of the general formula III

The two pairs of radicals $R^1/R^2$ are preferably identical. If, however, it is intended to prepare compounds I having different substituents at the 4 positions of the two piperidinyl rings, it is advantageous to start from mixtures of the starting compounds II.

The bridging members A as defined under (a) are preferably incorporated so that the particular oxygen atom or nitrogen atom is bonded directly to the piperidinyl ring. In the case of the urethane group —O—CO—NR$^5$—, O— and N-substitution are equally possible. Compounds I having a carbonyl function bonded directly to the 4 position of the piperidinyl ring may likewise be prepared by the novel process, but the corresponding starting compounds II are more difficult to synthesize than in the case of O— or N-substitution.

The present invention furthermore relates to a process for the preparation of N,N'-bridged bistetramethylpiperidinyl esters of the general formula Ib

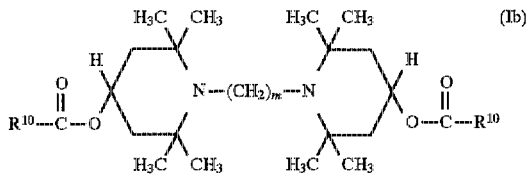

where m is 2 or 3 and R$^{10}$ is $C_1$–$C_{20}$-alkyl or $C_2$–$C_{20}$-alkenyl, which may be substituted by up to 3 hydroxyl groups, $C_1$–$C_{20}$-alkoxy, $C_3$–$C_{12}$-cycloalkyl, which may be substituted by up to 3 $C_1$–$C_4$-alkyl groups, phenyl which may be substituted by up to 3 $C_1$–$C_6$-alkyl groups or hydroxyl groups, or $C_7$–$C_{18}$-phenylalkyl which may be substituted by up to 3 $C_1$–$C_4$-alkyl groups or hydroxyl groups, wherein an N,N'-bridged bistetramethylhydroxypiperidinyl compound of the formula Ic

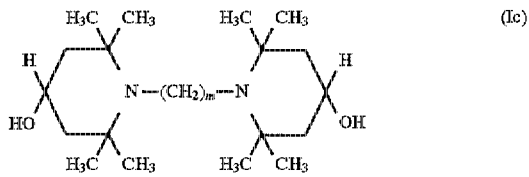

is reacted with a carboxylic acid derivative of the general formula R$^{10}$—CO—R$^{11}$, where R$^{11}$ is chlorine, bromine, $C_1$–$C_4$-alkoxy or a group of the formula —O—CO—R$^{10}$.

Examples of suitable straight-chain or branched alkyl radicals for R$^3$ to R$^6$ and R$^{10}$ and in R$^2$ as defined under (b) and as substituents on cycloaliphatic rings, on aromatic rings and on heterocyclic rings, which are referred to as $C_1$–$C_4$-alkyl, $C_1$–$C_6$-alkyl and $C_1$–$C_{20}$-alkyl radicals, are methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl, n-octadecyl, n-nonadecyl and n-eicosyl. $C_1$–$C_4$-alkyl radicals, in particular methyl and ethyl, are preferred among these, in particular as substituents on cycloaliphatic, aromatic and heterocyclic rings. Industrial or naturally occurring mixtures of different radicals of this type may also occur as alkyl radicals.

Alkyl radicals R$^3$ interrupted by non-neighboring oxygen atoms, bridging members —NR$^4$— and carbonyl groups are, for example, groups of the formula —(CH$_2$CH$_2$O)$_n$—CH$_2$CH$_3$ (n=1 to 9), —CH$_2$CH$_2$—N(CH$_3$)—CH$_2$CH$_3$, —CH$_2$CH$_2$—N(CH$_3$)—CH$_2$CH$_2$CH$_3$ and —CH$_2$CH$_2$—CO—CH$_3$.

Suitable straight-chain or branched $C_2$–$C_{20}$-alkenyl radicals for R$^3$, R$^4$, R$^6$ and R$^{10}$ and in R$^2$ as defined under (b) are, for example, vinyl, allyl, methallyl, 1-propenyl, 4-pentenyl, oleyl, linolyl and linolenyl. $C_2$–$C_5$-alkenyl and $C_{16}$–$C_{18}$-alkenyl are preferred here.

Suitable straight-chain or branched $C_1$–$C_{20}$-alkoxy radicals R$^{10}$ are in particular $C_1$–$C_4$-alkoxy. Among the $C_1$–$C_4$-alkoxy radicals R$^{10}$ and R$^{11}$, methoxy and ethoxy are particularly preferred.

Preferred unsubstituted or alkyl-substituted $C_3$–$C_{12}$-cycloalkyl radicals R$^3$, R$^4$ and R$^{10}$ are $C_5$–$C_8$-cycloalkyl, especially $C_5$- or $C_6$-cycloalkyl, such as cyclopentyl and cyclohexyl, as well as cycloheptyl, cyclooctyl, 2- or 3-methylcyclopentyl, 2,3-, 2,4-, 2,5- or 3,3-dimethylcyclopentyl, 2-, 3- or 4-methylcyclohexyl, 2-, 3- or 4-ethylcyclohexyl and 2,4-, 3,4-, 3,5- or 3,3-dimethylcyclohexyl, and furthermore cyclopropyl, cyclobutyl, cyclododecyl, 3,4,5-trimethylcyclohexyl or 4-tert-butylcyclohexyl.

Alkyl-substituted and hydroxyl-substituted phenyl radicals R$^3$ are, for example, o-, m- or p-tolyl, o-, m- or p-ethylphenyl, m- or p-tert-butylphenyl, 2,4,6-trimethylphenyl, 3,5-di-tert-butyl-4-hydroxyphenyl and o-, m- or p-hydroxyphenyl.

Suitable $C_7$–$C_{18}$-phenylalkyl radicals R$^3$, R$^4$ and R$^{10}$ are in particular 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 10-phenyldecyl, 12-phenyldodecyl and especially benzyl. Examples of suitable substituted $C_7$–$C_{18}$-phenylalkyl radicals are p-methylbenzyl, 2-(p-methylphenyl)ethyl, p-tert-butylbenzyl, 2-(p-tert-butylphenyl)ethyl and 2-(3',5'-di-tert-butyl-4'-hydroxyphenyl)ethyl.

$C_6$–$C_{18}$-Cycloalkylalkyl radicals R$^3$ and R$^4$ are, for example, cyclohexylmethyl, 4-methylcyclohexylmethyl, 4-tert-butylcyclohexylmethyl, 2-cyclohexylethyl, 3,3-dimethylcyclohexylmethyl and cyclopentylmethyl.

Suitable five-membered or six-membered unsaturated or saturated heterocyclic rings for R$^3$, having up to three hetero atoms selected from the group consisting of nitrogen, oxygen and sulfur which may additionally be benzofused and may be substituted by the radicals defined, are:

Tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imdidazole, 1,2,3-triazolidine, 1,2,3- and 1,2,4-triazole, 1,2, 3-, 1,2,4-, and 1,2,5-oxadiazole, tetrahydropyran, dihydropyran, 2H- and 4H-pyran, piperidine, 1,3- and 1,4-dioxane, morpholine, pyrazan, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chroman, isochroman, 2H- and 4H-chromene, quinoline, isoquinoline, 1,2,3,4-tetrahydroisoquinoline, cinnoline, quinazoline, quinoxaline, phthalazine and benzo-1,2,3-triazine.

The pair of radicals R1/R$^2$ may not contain any primary or secondary amino groups, since otherwise the cyclic carbonate III could also react with these amino groups and would give undesirable byproducts.

Examples of alkoxycarbonylalk(en)yloxy groups R$^2$ as defined under (b) are methoxycarbonylmethoxy, 2-(methoxycarbonyl)ethoxy, 2-(methoxycarbonyl) ethenyloxy and 2-(methoxycarbonyl)isopropenyloxy.

As defined under (c), the two radicals R$^6$ are preferably identical or, together with the two oxygen atoms, form a 1,3-dioxane or 1,3-dioxolane ring which may additionally carry lower alkyl and/or hydroxyalkyl as substituents. Examples of such cyclic acetal groups are 1,3-dioxane, 5-methyl-1,3-dioxane, 5,5-dimethyl-1,3-dioxane, 4,5,5-trimethyl-1,3-dioxane, 5-hydroxymethyl-5-methyl-1,3-dioxane, 5,5-bishydroxymethyl-1,3-dioxane, 1,3-dioxolane, 4-methyl-1,3-dioxolane and 4-hydroxymethyl-1,3-dioxolane groups.

The N,N'-bridged bistetramethylpiperidone compounds I as defined under (d) may also be present in etherified form as enol ethers of the general formula

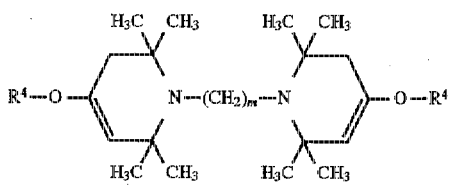

where the two radicals $R^4$ are identical or different and have the abovementioned meanings.

The N,N'-bridged bistetramethylhydroxypiperidinyl compounds Ic are obtainable by the reaction, according to the invention, of 2,2,6,6-tetramethylpiperidin-4-ol- [sic] with ethylene carbonate or 1,3-propylene carbonate. However, they may also be prepared by the method stated in the prior art.

Particularly suitable carboxylic acid derivatives $R^{10}$—CO—$R^{11}$ are the corresponding acyl halides, in particular acyl chlorides, the carboxylic esters, carboxylic anhydrides and diesters of carbonic acid, in particular dialkyl carbonates.

The novel process for obtaining product I is carried out, as a rule, at from 60° to 200° C., preferably from 100° to 180° C., in particular from 140° to 165° C. In the stated temperature range, the reaction is generally complete after from 5 to 25 hours. Since gaseous carbon dioxide is liberated during the reaction, it is advantageous to employ atmospheric or reduced pressure. In the novel process for obtaining product Ib, the conditions employed are as a rule the same as those stated for the preparation of the product I.

The reactions may be carried out in the presence or absence of solvent. Particularly suitable organic solvents are those which have a boiling point above 60° C., especially above 100° C., in particular above 140° C. Examples of these are:

- alcohols, such as methanol, ethanol, isopropanol, ethylene glycol, n-propanol, n-butanol, isobutanol, tert-butanol and in particular 2-ethylhexanol, n-octanol and diethylene glycol;
- amides, such as formamide, dimethylformamide, dimethylacetamide and in particular N-methylpyrrolidinone;
- aromatics, such as chlorobenzene, toluene, xylene, ethylbenzene and more highly alkylated benzenes;
- ethers, such as diisopropyl ether, di-n-propyl ether, diphenyl ether and tetrahydrofuran;
- tertiary amines, such as triethylamine, tributylamine and pyridine;
- polyethylene glycols or polypropylene glycols having a molecular weight up to about 1,000.

Mixtures of the stated organic solvents may also be used.

In a preferred embodiment, an excess of the cyclic carbonate III used as a reactant is employed as a solvent. In this case, the molar ratio of tetramethylpiperidinyl compound II to cyclic carbonate III is as a rule from 1:0.6 to 1:20, preferably from 1:1 to 1:10, in particular from 1:2 to 1:6, 0.5 mol of cyclic carbonate III being required per mol of starting compound II for the actual reaction.

It is also of [sic] advantageous, in the conversion of the alcohols Ic to the esters Ib, to use excess carboxylic acid derivative $R^{10}$—CO—$R^{11}$ as the solvent, particularly when carboxylic esters or diesters of carbonic acid are employed. In this case, the molar ratio of alcohol Ic to carboxylic acid derivative defined is as a rule from 1:2.1 to 1:50, preferably from 1:3 to 1:40.

A further preferred embodiment of the novel process is carried out with the aid of a catalyst. The catalyst is used in an amount of from 0.01 to 25, preferably from 0.5 to 10, in particular from 1 to 7, mol %, based on the amount of II or Ic. Increasing the amount of catalyst to above 25 mol % has no adverse effect on the reaction but offers no further advantages. The catalysts belong to the following classes:

(i) acidic catalysts, for example

- sulfonic acids, such as methanesulfonic acid, trifluoromethanesulfonic acid, benzenesulfonic acid or p-toluene-sulfonic acid;
- mineral acids (inorganic acids), such as sulfuric acid, hydrochloric acid or phosphoric acid;
- carboxylic acids, such as formic, acetic, propionic, butyric, valeric, caproic, caprylic, capric, stearic, oleic, benzoic, methylbenzoic, phenylacetic, citric, adipic, tartaric, nitrilotriacetic or ethylenediaminetetraacetic acid;

(ii) heavy metal-containing catalysts, for example

- tin compounds, such as dibutyltin oxide, dibutyltin diacetate or dibutyltin dilaurate;
- Titanates such as tetramethyl titanate, tetra-isopropyl titanate or tetrabutoxyy titanate;

(iii) organic catalysts having quaternized hetero atoms, for example

- phosphonium compounds, such as the chlorides, bromides or iodides of the cations methyltriphenylphosphonium, ethyltriphenylphosphonium, butyltriphenylphosphonium, methyltributylphosphonium, methyltriphenoxyphosphonium or tetrabutylphosphonium;
- ammonium compounds, such as the chlorides, bromides, iodides or hydroxides of the cations tetramethylammonium, tetraethylammonium, tetrabutylammonium, methyltriphenylammonium, methyltriethylammonium, methyltributylammonium, methyltrihexylammonium, benzyltriethylammonium, benzyltributylammonium, benzyltriphenylammonium or benzyltrihexylammonium;

(iv) halides, as a rule in anhydrous form, for example

- alkali metal halides, such as lithium iodide, sodium bromide, sodium iodide, potassium bromide or potassium iodide;
- alkaline earth metal halides, such as calcium chloride, magnesium chloride or magnesium bromide;
- zinc halides, such as zinc chloride, zinc bromide or zinc iodide.

The novel processes can be carried out particularly readily using ethylene carbonate (m=2 in formula III) as component III.

The novel process for obtaining product I also gives particularly good results if compounds II in which, according to the definition under (a), $R^1$ is hydrogen and $R^2$ is a group of the formula —OH, —NH—CO—$R^7$ or —O—CO—$R^7$, where $R^7$ is $C_1$–$C_4$-alkyl, are used as starting materials.

The present invention furthermore relates to N,N'-bridged bistetramethylpiperidinyl compounds of the general formula Ia

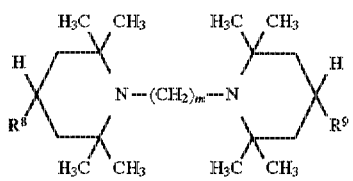

where m is 2 or 3, $R^8$ is a group of the formula —A—$R^3$,

A is oxygen or a bridging member of the formula —NR$^4$—, —NR$^5$—CO—, —O—CO—, —O—CO—NR$^5$— or O—CO—O—, $R^3$ is hydrogen or $C_1$–$C_{20}$-alkyl which may be interrupted by up to 10 non-neighboring oxygen atoms or bridging members of the formula —NR$^4$— and by up to 3 carbonyl groups, $C_2$–$C_{20}$-alkenyl, $C_3$–$C_{12}$-cycloalkyl which may be substituted by up to 3 $C_1$–$C_4$-alkyl groups, phenyl which may be substituted by up to 3 $C_1$–$C_6$-alkyl groups or hydroxyl groups, $C_7$–$C_{18}$-phenylalkyl which may be substituted by up to 3 $C_1$–$C_4$-alkyl groups or hydroxyl groups, $C_6$–$C_{18}$-cycloalkylalkyl which may be substituted by up to 3 $C_1$–$C_4$-alcohol [sic] groups, or a five-membered or six-membered unsaturated or saturated heterocyclic ring having up to 3 hetero atoms selected from the group consisting of nitrogen, oxygen and sulfur, which may additionally be benzofused and substituted by up to 3 $C_1$–$C_6$-alkyl groups or hydroxyl groups, with the proviso that $R^3$ is not hydrogen if A is the bridging member —NR$^4$—, $R^4$ is $C_1$–$C_{20}$-alkyl, $C_2$–$C_{20}$-alkenyl, $C_3$–$C_{12}$-cycloalkyl which may be substituted by up to 3 $C_1$–$C_4$-alkyl groups, $C_7$–$C_{18}$-phenylalkyl which may be substituted by up to 3 $C_1$–$C_4$-alkyl groups, or $C_6$–$C_{18}$-cycloalkylalkyl which may be substituted by up to 3 $C_1$–$C_4$-alkyl groups and $R^5$ is hydrogen or $C_1$–$C_4$-alkyl, and $R^9$ is a group of the formula —B—$R^3$, B is a bridging member of the formula —NR$^4$—, —NR$^5$—CO—, —O—CO—NR$^5$— or —O—CO—O— and $R^3$, $R^4$ and $R^5$ have the abovementioned meanings.

$R^8$ and $R^9$ are preferably identical. Regarding the position of the bridging members B, the statements made further above for the position of the bridging members A are applicable.

The novel compounds Ia as well as the compounds I and Ib are very suitable for stabilizing organic material to the effect of light, oxygen and heat. They are also effective as metal deactivators. They are added to the organic material to be stabilized in a concentration of from 0.01 to 5, preferably from 0.02 to 2, % by weight, based on the organic material, before, during or after its preparation.

Organic material is to be understood as meaning, for example, cosmetic preparations, such as ointments and lotions, drug formulations such as pills and suppositories, photographic recording materials, in particular photographic emulsions, and intermediates for plastics and coatings, but in particular plastics and coatings themselves.

The present invention also relates to organic materials stabilized to the effect of light, oxygen and heat, in particular plastics and coatings which contain the compounds Ia in the abovementioned concentrations.

All known apparatuses and methods for mixing stabilizers or other additives into polymers may be used for mixing the novel compounds Ia, especially with plastics.

The organic materials stabilized by the novel compounds Ia may, if required, contain further additives, for example antioxidants, light stabilizers, metal deactivators, antistatic agents, flame-retardant agents, pigments and fillers.

Antioxidants and light stabilizers which may be added in addition to the novel compounds Ia are, for example, compounds based on sterically hindered phenols or sulfur- or phosphorus-containing costabilizers.

Examples of such phenolic antioxidants are 2,6-di-tert-butyl-4-methylphenol, n-octadecyl β-(3,5-di-tert-butyl-4-hydroxyphenyl)propionate, 1,1,3-tris-(2-methyl-4-hydroxy-5-tert-butylphenyl)butane, 1,3,5-trimethyl-2,4,6-tris-(3,5-di-tert-butyl-4-hydroxybenzyl)benzene, 1,3,5-tris-(3,5-di-tert-butyl-4-hydroxybenzyl) isocyanurate, 1,3,5-tris-[β-(3,5-di-tert-butyl-4-hydroxybenzyl)propionylethyl] isocyanurate, 1,3,5-tris-(2,6-dimethyl-3-hydroxy-4-tert-butylbenzyl) isocyanurate and pentaerythrityl tetrakis-[β-3,5-di-tert-butyl-4-hydroxyphenyl)propionate].

Examples of suitable phosphorus-containing antioxidants are tris-(nonylphenyl) phosphite, distearyl pentaerythrityl diphosphite, tris-(2,4-di-tert-butylphenyl) phosphite, distearyl pentaerythrityl diphosphite [sic], tris-(2-tert-butyl-4-methylphenyl) phosphite, bis-(2,4-di-tert-butylphenyl) pentaerythrityl diphosphite and tetrakis-(2,4-di-tert-butylphenyl) 4,4'-biphenylene diphosphite.

Examples of sulfur-containing antioxidants are dilauryl thiodipropionate, dimyristyl thiodipropionate, distearyl thiodipropionate, pentaerythrityl tetrakis-β-laurylthiopropionate) and pentaerythrityl tetrakis-(β-hexylthiopropionate). Thiobisphenols, such as 3,3'-di-tert-butyl-4,4'-dihydroxy-2,2'-dimethyldiphenyl sulfide, may also be added.

Further antioxidants and light stabilizers which may be used together with the novel compounds Ia are, for example, 2-(2'-hydroxyphenyl)benztriazoles, 2-hydroxybenzophenones, aryl esters of hydroxybenzoic acids, α-cyanocinnamic acid derivatives, benzimidazolecarboxanilides, nickel compounds and oxalic acid dianilides.

Particularly good stabilization is obtained if at least one further light stabilizer from the class consisting of the sterically hindered amines is also added, in the usual concentration, to the novel compounds Ia.

Examples of further sterically hindered amines suitable for this purpose are bis-(2,2,6,6-tetramethylpiperidyl) sebacate, bis-(1,2,2,6,6-pentamethylpiperidyl) sebacate, the condensate of 1-hydroxyethyl-2,2,6,6-tetramethyl-4-hydroxypiperidine with succinic acid, the condensate of N,N'-(2,2,6,6-tetramethylpiperidyl)hexamethylenediamine with 4-tert-octylamino-2,6-di-chloro-1,3,5-triazine, tris-(2,2,6,6-tetramethylpiperidyl) nitrilotriacetate, tetrakis-(2,2,6,6-tetramethyl-4-piperidyl) 1,2,3,4-butanetetracarboxylate, 1,1'-(1,2-ethanediyl)-bis-(3,3,5,5-tetramethylpiperazinone) and the condensates of 4-amino-2,2,6,6-tetramethylpiperidines [sic] with tetramethylolacetylenediureas.

Examples of plastics which may be stabilized by means of the novel compounds Ia are:

Polymers of mono- and diolefins, for example low density or high density polyethylene, polypropylene, linear polybut-1-ene, polyisoprene, polybutadiene and copolymers of mono- or diolefins or mixtures of the stated polymers;

Copolymers of mono- or diolefins with other vinyl monomers, for example ethylene/alkyl acrylate copolymers, ethylene/alkyl methacrylate copolymers, ethylene/vinyl acetate copolymers or ethylene/acrylic acid copolymers;

Polystyrene and copolymers of styrene or α-methylstyrene with dienes and/or acryloyl derivatives, for example styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

Halogen-containing polymers, for example polyvinyl chloride, polyvinyl fluoride, polyvinylidene fluoride and copolymers thereof;

Polymers which are derived from $\alpha,\beta$-unsaturated acids and derivatives thereof, such as polyacrylates, polymethacrylates, polyacrylamides and polyacrylnitriles;

Polymers which are derived from unsaturated alcohols and amines or from acryloyl derivatives or acetals thereof, for example polyvinyl alcohol and polyvinyl acetate;

Polyurethanes, polyamides, polyureas, polyphenylene ethers, polyesters, polycarbonates, polysulfones, polyethersulfones and polyetherketones.

Coatings, for example industrial coatings, may also be stabilized with the novel compounds Ia. These coatings include baking finishes, among which in turn vehicle finishes, preferably two-coat finishes, are particularly noteworthy.

The novel compounds Ia may be added to the coating in solid or dissolved form. Their good solubility in coating systems is particularly advantageous.

The novel compounds Ia are preferably used for stabilizing polyamides as well as ABS and SAN polymers, in particular for stabilizing molding materials produced therefrom, and for stabilizing coatings. A further preferred field of use is the stabilization of polypropylene and polyamide.

The novel compounds Ia are highly compatible with the conventional types of plastics and have good solubility and excellent compatibility in the conventional coating systems. They have, as a rule, very little or no natural color, are stable at the usual temperatures for processing plastics and coatings, are nonvolatile and in particular provide protection over a long period for the materials treated with them.

The examples which follow illustrate the invention. The preparation conditions were not optimized.

PREPARATION EXAMPLES

Example 1

628 g (4.0 mol) of 2,2,6,6-tetramethylpiperidin-4-ol, 880 g (10.0 mol) of ethylene carbonate and 30 g (0.08 mol) of tetrabutylammonium iodide were heated for 13 hours at 155° C. and for a further 6 hours at 165° C., $CO_2$ being eliminated. The mixture was left to cool, and 1 l of water was slowly added with evaporative cooling to 130° C. Thereafter, the stirred mixture was left to cool, and the resulting precipitate was filtered off with suction at room temperature and washed with water until the filtrate was colorless. Drying gave 603 g of the compound of the formula

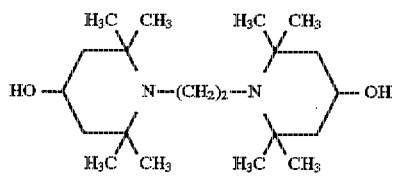

as a colorless solid of melting point 264°–267° C.

Example 2

49.5 g (0.23 mol) of 4-N-acetyl-2,2,6,6-tetramethyl-4-aminopiperidine, 100 g (1.14 mol) of ethylene carbonate and 5 g (0.14 mol) of tetrabutylammonium iodide were heated for 7 hours at 155° C., $CO_2$ being eliminated. The mixture was left to cool, 150 mol of water were added, stirring was carried out for 2 hours at 90° C. and the resulting precipitate was filtered off with suction at this temperature. The residue was washed with twice 100 ml of ethanol and dried at 50° C. under reduced pressure from a water pump. 37.6 g of the compound of the formula

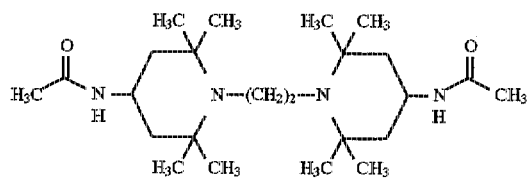

of melting point >300° C. were obtained.

Example 3

51 g of the product from Example 1, 1.5 ml of dibutyltin diacetate and 400 g of diethyl carbonate were stirred for 30 hours at 125° C., ethanol distilling off. The mixture was diluted with petroleum ether, the residue was taken up in 1.8 l of ethanol and the mixture was filtered while hot and left to cool. Filtration and drying gave 33.4 g of the compound of the formula

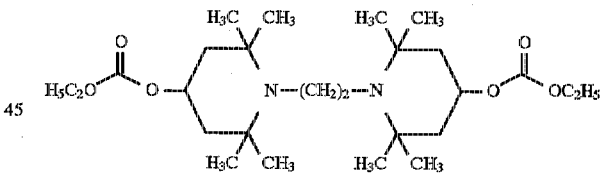

as a colorless solid of melting point 187°–188° C.

Example 4

34 g of the product from Example 1, 64.4 g of methyl 3-(3',3'-di-tert-butyl-4'-hydroxyphenyl)propionate and 1.5 ml of dibutyltin diacetate in 150 ml of Solvesso® 100 (commercial mixture of aromatic hydrocarbons having a boiling range of from 163° to 170° C.) were heated at 170° C. for 14 hours, methanol distilling off. Thereafter the solvent was distilled off under reduced pressure and the residue was recrystallized from methylcyclohexane. Filtration and drying gave 46 g of the compound of the formula

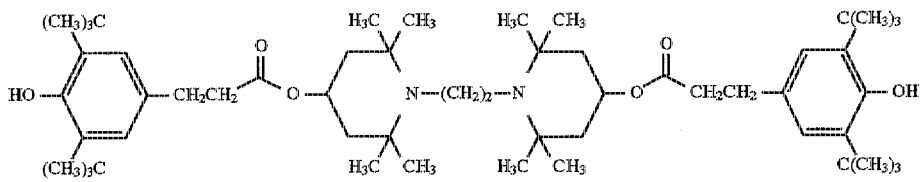

as a colorless solid of melting point 207°–208° C.

Example 5

Synthesis of the compound from Example 1 using various catalysts under standardized conditions 31.4 g of 2,2,6,6-tetramethylpiperidin-4-ol, 44 g of ethylene carbonate and 0.5 g of a catalyst according to Table 1 were heated for 7 hours at 150°–155° C. Thereafter, the mixture was cooled to 90° C. and 150 ml of water were added dropwise. The mixture was refluxed for 0.5 hour and the resulting precipitate was filtered off at 95° C. The product was washed with 50 ml of water at 90° C. and dried at 110° C. under reduced pressure from a water pump.

The product yields obtained are listed in the table.

Table

Reaction of 2,2,6,6-tetramethylpiperidin-4-ol with ethylene carbonate using various catalysts

| Catalyst | Yield [%] |
|---|---|
| Lithium iodide | 89.4 |
| Sodium bromide | 83.2 |
| Sodium iodide | 85.3 |
| Potassium bromide | 64.1 |
| Potassium iodide | 60.2 |
| Magnesium chloride | 80.0 |
| Magnesium bromide | 90.9 |
| Tetrabutylammonium bromide | 55.3 |
| Tetrabutylammonium iodide | 57.9 |
| Tetraethylammonium iodide | 50.9 |
| Tetramethylammonium iodide | 60.3 |
| Methyltriphenylphosphonium iodide | 75.3 |
| Methyltriphenoxyphosphonium iodide | 83.5 |

We claim:

1. A process for the preparation of N,N'-bridged bistetramethypiperidinyl compounds of the formula I

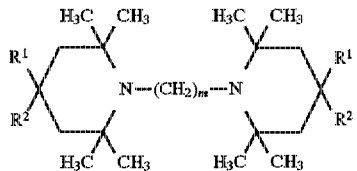

where m is 2 or 3 and the two pairs of radicals $R^1/R^2$ are identical or different and may have the following meanings:

(a)

$R^1$ is hydrogen and $R^2$ is a group of the formula —A—$R^3$, A is oxygen or a bridging member of the formula —$NR^4$—, —$NR^5$—CO—, —O—CO—, —O—CO—$NR^5$— or O—CO—O—, $R^3$ is hydrogen or $C_1$–$C_{20}$-alkyl which may be interrupted by up to 10 non-neighboring oxygen atoms or bridging members of the formula —$NR^4$— and by up to 3 carbonyl groups, $C_2$–$C_{20}$-alkenyl, $C_3$–$C_{12}$-cycloalkyl which may be substituted by up to 3 $C_1$–$C_4$-alkyl groups, phenyl which may be substituted by up to 3 $C_1$–$C_6$-alkyl groups or hydroxyl groups, $C_7$–$C_{18}$-phenylalkyl which may be substituted by up to 3 $C_1$–$C_4$-alkyl groups or hydroxyl groups, $C_6$–$C_{18}$-cycloalkylalkyl which may be substituted by up to 3 $C_1$–$C_4$-alkyl groups, or a five-membered or six-membered unsaturated or saturated heterocyclic ring having up to 3 hetero atoms selected from the group consisting of nitrogen, oxygen and sulfur, which may additionally be benzofused and substituted by up to 3 $C_1$–$C_6$-alkyl groups or hydroxyl groups, with the proviso that $R^3$ is not hydrogen if A is the bridging member —$NR^4$—, $R^4$ is $C_1$–$C_{20}$-alkyl, $C_2$–$C_{20}$-alkenyl, $C_3$–$C_{12}$-cycloalkyl which may be substituted by up to 3 $C_1$–$C_4$-alkyl groups, $C_7$–$C_{18}$-phenylalkyl which may be substituted by up to 3 $C_1$–$C_4$-alkyl groups, or $C_6$–$C_{18}$-cycloalkylalkyl which may be substituted by up to 3 $C_1$–$C_4$-alkyl groups and $R^5$ is hydrogen or $C_1$–$C_4$-alkyl;

(b)

$R^1$ is hydrogen and $R^2$ is $C_1$–$C_6$-alkoxycarbonyl-$C_1$–$C_{20}$-alkyloxy or $C_1$–$C_6$-alkoxycarbonyl -$C_2$–$C_{20}$-alkenyloxy;

(c)

$R^1$ and $R^2$ are each a group of the formula —O—$R^6$, where the two radicals $R^6$ are identical or different and are each $C_1$–$C_{20}$-alkyl or $C_2$–$C_{20}$-alkenyl, which may be substituted by up to 3 hydroxyl groups, and may be linked to form a 1,3-dioxane or a 1,3-dioxolane ring;

(d)

$R^1/R^2$ is the carbonyl oxygen atom of a piperidone ring, where these oxygen atoms may furthermore be etherified by groups of the structure $R^4$ to form the corresponding enol structure on the piperidone ring;

starting from tetramethylpiperidinyl compounds of the formula II

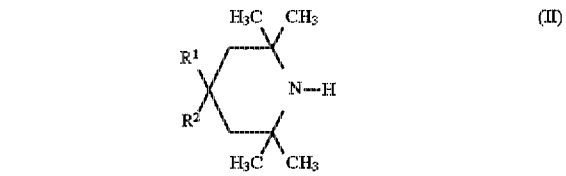

which comprises reacting a compound II with a cyclic carbonate of the formula III

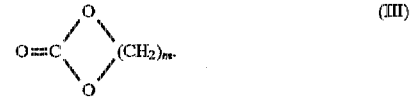

2. A process for the preparation of N,N'-bridged bistetramethylpiperidinyl compounds I as claimed in claim 1, wherein an excess of the cyclic carbonate III is used as the solvent, the molar ratio of II to III being from 1:0.6 to 1:20.

3. A process for the preparation of N,N'-bridged bistetramethylpiperidinyl compounds I as claimed in claim 1, wherein the reaction is carried out in the presence of from 0.01 to 25 mol %, based on the amount of tetramethylpiperidinyl compound II used, of an acidic catalyst, of a heavy-metal-containing catalyst, of an organic catalyst having a quaternized hetero atom or of a halide as the catalyst.

4. A process for the preparation of N,N'-bridged bistetramethylpiperidinyl compounds I as claimed in claim 1, wherein ethylene carbonate is used as the cyclic carbonate III.

5. A process for the preparation of N,N'-bridged bistetramethylpiperidinyl esters of the formula Ib

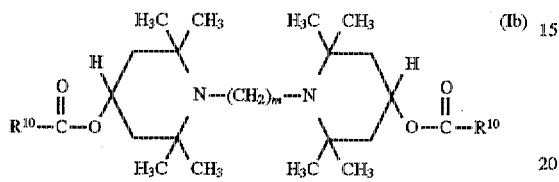

where m is 2 or 3 and $R^{10}$ is $C_1$–$C_{20}$-alkyl or $C_2$–$C_{20}$-alkenyl, which may be substituted by up to 3 hydroxyl groups, $C_1$–$C_{20}$-alkoxy, $C_3$–$C_{12}$-cycloalkyl, which may be substituted by up to 3 $C_1$–$C_4$-alkyl groups, phenyl which may be substituted by up to 3 $C_1$–$C_6$-alkyl groups or hydroxyl groups, or $C_7$–$C_{18}$-phenylalkyl which may be substituted by up to 3 $C_1$–$C_4$-alkyl groups or hydroxyl groups, wherein an N,N'-bridged bistetramethylhydroxypiperidinyl compound, prepared according to the process as claimed in claim 1, of the formula Ic

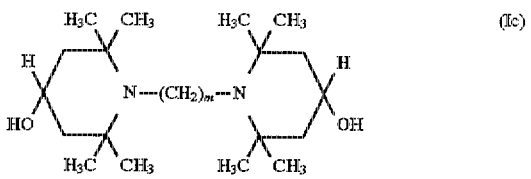

is reacted with a carboxylic acid derivative of the general formula $R^{10}$—CO—$R^{11}$, where $R^{11}$ is chlorine, bromine, $C_1$–$C_4$-alkoxy or a group of the formula —O—CO—$R^{10}$.

6. A process for the preparation of N,N'-bridged bistetramethylpiperidinyl esters Ib as claimed in claim 5, wherein an excess of the carboxylic acid derivative used as a reactant is employed as the solvent, the molar ratio of Ic to carboxylic acid derivative being from 1:2.1 to 1:50.

7. A process for the preparation of N,N'-bridged bistetramethylpiperidinyl esters Ib as claimed in claim 5, wherein the reaction is carried out in the presence of from 0.01 to 25 mol %, based on the amount of alcohol Ic used, of an acidic catalyst, of a heavy-metal-containing catalyst, of an organic catalyst having a quaternized hetero atom or of a halide as catalyst.

8. A process for the preparation of N,N'-bridged bistetramethylpiperidinyl compounds of the formula I starting from tetramethylpiperidinyl compounds of the formula II:

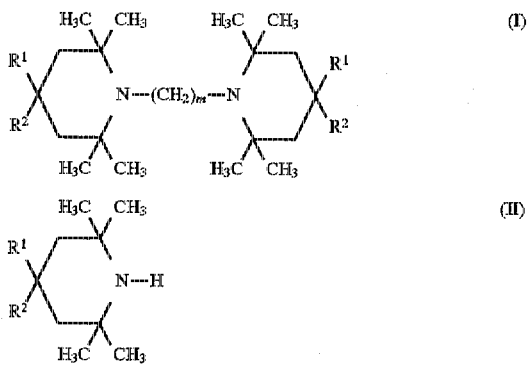

which comprises reacting a compound II with a cyclic carbonate of the formula III:

wherein:

m is 2 or 3;

$R^1$ is hydrogen; and $R^2$ is —OH, —NH—CO—$R^7$ or —O—CO—$R^7$, wherein $R^7$ is $C_1$–$C_4$-alkyl.

* * * * *